United States Patent [19]
Hellstrand et al.

[11] Patent Number: 5,728,378
[45] Date of Patent: Mar. 17, 1998

[54] PREPARATION FOR ACTIVATION OF NATURAL KILLER CELLS (NK-CELLS), SAID PREPARATION CONTAINING INTERFERON-ALPHA AND HISTAMINE, SEROTONIN, AMINES OR SUBSTANCES WITH CORRESPONDING RECEPTOR ACTIVITY

[75] Inventors: Kristoffer Hellstrand, Göteborg; Svante Hermodsson, Mölndal, both of Sweden

[73] Assignee: Maxim Pharmaceuticals, Inc., San Diego, Calif.

[21] Appl. No.: 374,787

[22] PCT Filed: Jun. 3, 1993

[86] PCT No.: PCT/SE93/00496

§ 371 Date: May 8, 1995

§ 102(e) Date: May 8, 1995

[87] PCT Pub. No.: WO93/24144

PCT Pub. Date: Dec. 9, 1993

[30] Foreign Application Priority Data

Jun. 3, 1992 [SE] Sweden ............... 9201719

[51] Int. Cl.$^6$ ............... A61K 37/66
[52] U.S. Cl. ............... 424/85.7; 424/85.4; 530/351
[58] Field of Search ............... 514/370; 424/85.4, 424/85.7; 530/351; 546/67, 69; 548/335.5, 355.1, 375.1

[56] References Cited

U.S. PATENT DOCUMENTS

| | | | |
|---|---|---|---|
| 4,863,727 | 9/1989 | Zimmerman et al. | 424/85.2 |
| 4,883,661 | 11/1989 | Daly et al. | 424/85.2 |
| 4,997,645 | 3/1991 | Suzuki et al. | 424/85.5 |
| 5,026,544 | 6/1991 | Albrecht et al. | 424/85.4 |
| 5,215,744 | 6/1993 | Suzuki et al. | 424/85.4 |

OTHER PUBLICATIONS

Hellstrand et al., "Histamine H2–Receptor Mediated Regulation of Human Natural Killer Cell Activity", Journal of Immunology 137(2), Issued Jul. 15, 1986, pp. 656–660.

Hellstrand et al., "Enhancement of Human Natural Killer Cell Cytotoxicity by Serotonin: Role of Non–T/CD16+NK Cells, Accessory Monocytes, and 5–HT1A Receptors", Cellular Immunology, vol. 127, Issued 1990, pp. 199–214.

Chun, Myung et al. Modulation of Interferon–Induced NK Cells by Interleukin 2 and cAMP. Lymphokine Research, vol. 1, No. 4, pp. 91–98, (1982). Abstract Only.

"Enhancement of Human Natural Killer Cell Cytotoxicity by Serotonin: Role of Non–T/CD16 NK Cells, Accessory Monocytes, and 5–HT$_{1A}$ Receptors".

Hellstrand, et al., Cellular Immunology. 127:199–214, 1990.

"The Influence of Intraperitoneal Injections of Histamine on Tumour Growth in Fibrosarcoma–Bearing Mice" Burtin, et al., Cancer Letters, 12: 195–201, Jan. 1981.

"Successful Tumour Immunotherapy with Cimetidine in Mice" Osband, et al., The Lancet, No. 8221, 1: 636–638, Mar. 21, 1981.

(List continued on next page.)

Primary Examiner—John C. Bleutge
Assistant Examiner—Robert H. Harrison
Attorney, Agent, or Firm—Knobbe, Martens, Olson & Bear, LLP

[57] ABSTRACT

Pharmaceutical preparation or system for activation of natural killer cells (NK cells), for example in order to treat tumors or virus infections, and which comprises a first composition containing interferon-α or analogues thereof, together with a second composition containing at least one substance with $H_2$- or $5-HT_{1A}$- receptor agonist activity, for example, histamine or serotonin. The first and second compositions are either mixed in a preparation or furnished in separate doses.

15 Claims, 2 Drawing Sheets

OTHER PUBLICATIONS

"Suppression of Natural Killing in Vitro by Monocytes and Polymorphonuclear Leukocytes" Seaman, et al., *The Journal of Clinical Investigation*, 69: 876–888, Apr. 1982.

"The Differential Effects of Human Leukocytic Pyrogen/Lymphocyte–Activating Factor, T Cell Growth Factor, and Interferon on Human Natural Killer Activity" Dempsey, et al., *The Journal of Immunology*, May 17, 1982.

"Tumor–Enhancing Effects of Cimetidine" Barna, et al., *Oncology*, 40: 43–45, 1983.

"Combination of Cimetidine with other Drugs for Treatment of Cancer" Thornes, et al., *New England Journal of Medicine* 308: 591–592, Mar. 10, 1983.

"The Influence of Histamine of Immune and Inflammatory Responses " Beer, et al., *Advances in Immunology*, 35: 209–268, 1984.

"Enhancement by serotonin of intra–tumour penetration of spleen cells" Lespinatas, et al., *Br. J. Cancer*, 50: 545–547, Apr. 5, 1994.

"Histamine Inhibits Interferon–γProduction via Suppression of Interleukin 2 Synthesis" Dohlsten, et al., *Cellular Immunology*, 101: 493–501, 1986.

"Histamine–Induced Suppressor Factor Inhibition of NK Cells: Reversal with Interferon and Interleukin 2" Nair, et al., *The Journal of Immunology*, 136: No. 7, 2456–2462, Apr. 1, 1986.

"Histamine $H_2$–Receptor–Mediated Regulation of Human Natural Killer Cell Activity" Hellstrand, et al., *The Journal of Immunology*, 137: No. 2, Jul. 15, 1986.

"Biogenic Amines in the Regulation of Human Natural Killer Cell Cytotoxicity" Hellstrand, Published by Medi Press Research Reports, Printed by Novum Grafiska AB, Göteborg 1987.

"Differential Effects of Histamine Receptor Antagonists on Human Natural Killer Cell Activity" Hellstrand, et al., *Int. Archs Allergy appl. Immunology*, 84: 247–255, 1987.

"Selective, Histamine–Mediated Immunosuppression in Laryngeal Cancer" Richtsmeier, et al., *Ann Otol Rhinol Laryngol*, 96: No. 5, 569–572, 1987.

"Clinical Improvement in Advanced Cancer Disease After Treatment Combining Histamine and H2–Antihistaminics (Ranitidine or Cimetidine)" Burtin, et al., Accepted Jun. 1987.

"Role of Serotonin the Regulation of Human Natural Killer Cell Cytotoxicity" Hellstrand, et al., *The Journal of Immunology*, 139: No. 3, Aug. 1, 1987.

"Enhancement of Natural Killer Activity in Human Peripheral Blood by Flavone Acetic Acid" Urba, et al., *The Journal of the National Cancer Institute*, 80: No. 7, 521–525, Jun. 1, 1988

"Augmentation of Natural Killer Activity, Induction of IFN and Development Tumor Immunity During the Successful Treatment of Established Murine Renal Cancer Using Flavone Acetic Acid and IL–2" Hornung, et al., *The Journal of Immunology*, 141: No. 10, 3671–3679, Nov. 15, 1988.

"Enhancement of Human Natural Killer Cell Function by the Combined Effects of Tumor Necrosis Factor α or Interleukin–1 and Interferon–α or Interleukin–2" Østensen, et al., *Journal of Biological Response Modifiers*, 8: 53–61, 1989.

"Suppression of human natural killer cell cytotoxicity by interleukin–2" Hellstrand, et al., *Clin. Exp. Immunol*, 77: 410–416, 1989.

"Comparative Effect of Recombinant IL–1, –2, –3, –4, and –6, IFN–γ, Granulocyte–Macrophage–Colony–Stimulating Factors, Tumor Necrosis Factor–α, and Histamine–Releasing Factors on the Secretion of Histamine from Basophils" Alam, et al., *The Journal of Immunology*, 142: No. 10, 3431–3435, May 18, 1989.

"Regulation of Human Basophil Mediator Release by Cytokines" Schleimer, et al., *The Journal of Immunology*, 143: No. 4, 1310–1317, Aug. 15, 1989.

"A Cell–to–Cell Mediated Interaction Involving Monocytes and Non _T/CD16+Natural Killer (NK) Cells is Required for Histamine $H_2$–Receptor–Mediated NK–Cell Activation" Hellstrand, et al., *Scand J. Immunol*, 31: 631–644, 1990.

"Enhancement of Human Natural Killer Cell Cytotoxicity by Serotonin: Role of Non–T/CD16+NK Cells, Accessory Monocytes, and $5-HT_{1A}$ Receptors" Hellstrand, et al., *Cellular Immunology*, 127: 199–214, 1990.

"Monocyte–Mediated Suppression of IL–2–Induced NK–Cell Activation" Hellstrand, et al., *Scand J. Immunol*, 32: 183–192, 1990.

"Synergistic Activation of Human Natural Killer Cell Cytotoxicity by Histamine and Interleukin–2" Hellstrand, et al., *Int. Arch. Allergy Appl. Immunology*, 92: 379–389, 1990.

"Histamine Type 2–Receptor Antagonists and Cancer Immunotherapy" Tom Smith, MD, *Comprehensive Therapy*, 16: No. 1, 8–13, 1990.

"Renal Cell Carcinoma: Treatment with Recombinant Interleukin–2 Plus Beta–Interferon" Krigel, et al., *Journal of Clinical Oncology*, 8: No. 3, 460–467, Mar. 1990.

"Role of Histamine in Natural Killer Cell–Mediated Resistance Against Tumor Cells" Hellstrand, et al., *The Journal of Immunology*, 145: No. 12, Dec. 15, 1990.

"Cell–to–Cell Mediated Inhibition of Natural Killer Cell Proliferation by Monocytes and its Regulation by Histamine $H_2$–Receptors" Hellstrand, et al., *Scand J. Immunol*, 34: 741–752, 1991.

"Monocyte–Induced Down–Modulatio of CD16 and CD56 Antigens on Human Natural Killer Cells and its Regulation by Histamine $H_2$–Receptors" Hellstrand, et al., *Cellular Immunology*, 138: 44–45, 1991.

"A phase II study of interleukin–2 and interferon–alpha in head and neck cancer" Schantz, et al., *Investigational New Drugs*, 10: 217–223, 1992.

"Regulation of the Natural Killer Cell Response to Interferon–α by Biogenic Amines" Hellstrand, et al., *Journal of Interferon Research*, 12: 199–206, 1992.

"Phase I Trial of High–Dose Bolus Interleukin–2 and Interferon Alfa–2a in Patients with Metastatic Malignancy" Budd, et al., *Journal of Clinical Oncology*, 10: No. 5, 804–809, May 1992.

"A Phase II Trial of Interleukin–2 and Interferon Alfa–2a in Patients with Advanced Renal Cell Carcinoma" Ilson, et al., *Journal of Clinical Oncology*, 10: No. 7, 1124–1130, Jul. 1992.

"Effects of histamine type–2 receptor antagonists on indomethacin and IL–2 immunotherapy of metastasis" Saarloos, et al., *Clin. Exp. Metastasis*, 11: 275–283, 1993.

"Serotonergic $5-HT_{1A}$ Receptors Regulate a Cell Contact–Mediated Interaction between Natural Killer Cells and Monocytes" Hellstrand, et al., *Scand J. Immunol*, 37: 7–18, 1993.

"Histamine in immunotherapy of advanced melanoma: a pilot study" Hellstrand, et al., *Cancer Immunol Immunother*, 39: 416–419, 1994.

PREPARATION FOR ACTIVATION OF NATURAL KILLER CELLS (NK-CELLS), SAID PREPARATION CONTAINING INTERFERON-ALPHA AND HISTAMINE, SEROTONIN, AMINES OR SUBSTANCES WITH CORRESPONDING RECEPTOR ACTIVITY

FIELD OF THE INVENTION

The present invention concerns a pharmaceutical preparation or system for activation of natural killer cells (NK-cells), in order for example, to treat tumors or virus infections.

BACKGROUND OF THE INVENTION

Natural killer cells (NK-cells) are a group of spontaneously cytotoxic lymphocytes that destroy tumor cells by lysis with no antigen specificity or restriction by histocompatibility molecules. Monocytes are involved in the regulation of the NK-cell's function, both through mechanisms involving cell contact and through providing soluble NK cell-regulating mediators. Recently, a cell contact-mediated mechanism has been described whereby monocytes regulate NK-cells. This type of monocyte-mediated regulation is exerted by monocytes that are obtained directly from peripheral blood through counterflow centrifugal elutriation (CCE) and is regulated by the biogenic amines histamine and serotonin (Hellstrand and Hermodsson, 1986, J. Immunol. 137, 656–660; Hellstrand and Hermodsson, 1987, J. Immunol. 139, 869–875; Hellstrand and Hermodsson, 1990, Scand. J. Immunol. 31, 631–645; Hellstrand and Hermodsson, 1990, Cell. Immunol. 127, 199–214; Hellstrand, Kjellson and Hermodsson, 1991, Cell. Immunol., 138, 44–54). These NK-cell regulating mechanisms caused by biogenic amines should be of importance to the NK cell-mediated defence against metastatic tumors in vivo (Hellstrand, Asea and Hermodsson (1990), J. Immunology 145, 4365–4370).

Interferon-α (IFN-α) is an important regulating factor for NK cells. It effectively enhances the NK cell's cytotoxicity (NKCC) both in vivo and in vitro (Trinchieri, 1989, Adv. immunol. 47, 187–376; Einhorn, Blomgren and Strander, 1978, Int. J. Cancer 22, 405–412; Friedman and Vogel, 1984, Adv. Immunol., 34, 97–140).

Owing to the high rate of cancer and the only partially successful treatment methods available today, there is a constant demand for other improved methods of treatment of tumors. There is also a great demand for improved treatment methods for virus infections.

SUMMARY OF THE INVENTION

The goal of the invention is to create a pharmaceutical preparation or system that effectively stimulates NK cells, e.g., in order to treat tumors, primarily myelomas, renal cancer, leukemias and melanoma, or to treat virus infections, primarily chronic hepatitis B and hepatitis C. The preparation or system according to the invention involves a first composition, containing interferon-α or analogues thereof, and a second composition containing at least one substance with histamine $H_2$, or serotonin 5-$HT_{1A}$-receptor agonist activity, whereby said first and second compositions are either mixed in a preparation or supplied in separate doses in an amount sufficient for the intended treatment. The invention also comprises a method for treatment of viral or neoplastic disease comprising the step of coadministering to an animal, including a human, an effective amount of a histamine $H_2$ receptor agonist or a secotonin 5-$HT_{1A}$ receptor agonist. Furthermore, the invention includes use of a histamine $H_2$ receptor agonist or a 5-$HT_{1A}$ receptor agonist in the preparation of a medicament for treatment of viral or neoplastic disease by coadministration with interferon-α, as well as the use of interferon-α in the preparation of a medicament for treatment of neoplastic or viral disease by coadministration with a histamine $H_2$ receptor agonist or a serotonin 5-$HT_{1A}$ receptor agonist.

The invention shall be described in greater detail below, making reference to reported in vitro experiments.

DESCRIPTION OF THE INVENTION

Figure 1:
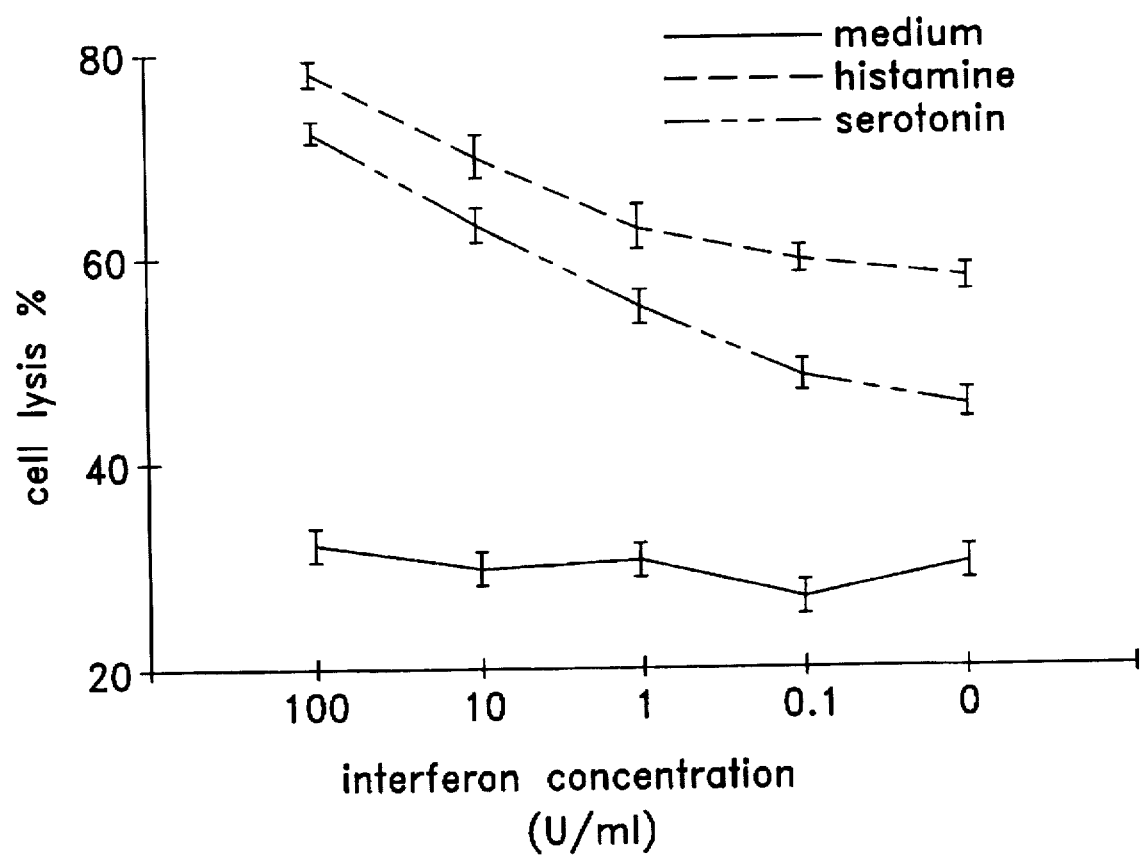
FIG. 1 shows in graph form the synergistic NK cell activation against cultured target cells produced by IFN-a and histamine or serotonin for various concentrations of IFN-α (0–100 U/ml).

The invention is based on the unexpected discovery in vitro that IFN-α and the biogenic amines histamine and/or serotonin produce a synergistic activation of NK cells.

The experiments reported hereafter show that eluted monocytes effectively suppress the activation of NK cells induced by IFN-α. Furthermore, it is shown that histamine or serotonin, which act through defined bioaminergic receptors, remove the monocyte-induced suppression and thereby restore the ability of the NK cells to respond to IFN-α.

Analogues of histamine with $H_2$-receptor agonist activity or other compounds with $H_2$-receptor agonist activity and analogues of serotonin with 5-$HT_{1A}$-receptor agonist activity or other compounds with 5-$HT_{1A}$-receptor agonist activity that are suitable for use in the present invention are known within the art and shall not be described more closely here. For example, these analogues can have a chemical structure resembling that of histamine or serotonin, but modified by addition of groups that do not negatively affect the $H_2$ or 5-$HT_{1A}$ receptor activities. Known $H_2$-receptor agonists include histamine, dimaprit, clonidine, tolazoline, impromadine, 4-methylhistamine, betazole and histamine congener derivatives such as

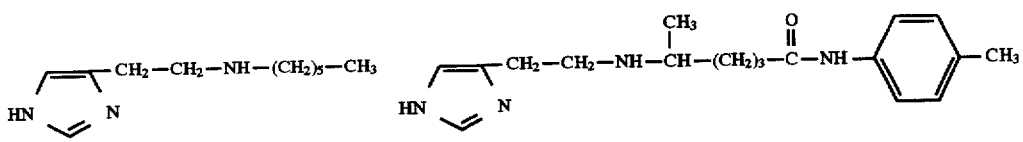

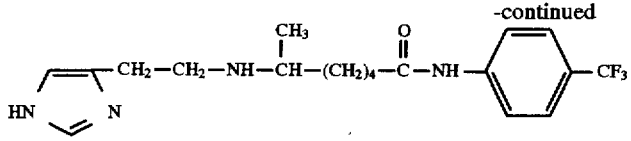

described as compounds 1, 6, and 9 in Khan et al., J. Immunol., Vol 137 pp 308–315. Known serotonin 5-$HT_{1A}$-receptor agonists include 8-OH-DPAT (8-hydroxy-2-(di-n-propylamino)tetralin), ALK-3 (cis-8-hydroxy-1-methyl-2-(di-n-propylamino)tetralin), BMY 7378 (8[2-[4-(2-methoxyphenyl)-1-piperazinyl]ethyl]-8azaspiro[4,5]decane-7,9-dione), NAN 190 (1-(2-methoxyphenyl)-4-[4-(2-phthalimmido)butyl]piperazine HBr), lisuride, d-LSD, flesoxinan, DHE (dihydroergotamine), MDL 72832 (8-[4-(1,4-benzodioxan-2-ylmethyl-amino)butyl]-8-azaspiro[4,5]decane-7,9-dione), 5-CT (5-carboxamidotryptamine), DP-5-CT (N,N-dipropyl-5-carboxamidotryptamine), ipsapirone, WB 4101 (2-[[[2-(2,6-dimethoxyphenoxy)ethyl]amino]methyl]-1,4-benzodioxane), ergotamine, buspirone, metergoline, spiroxatrine, PAPP (1-[2-(4-aminophenyl)ethyl]-4-(3-trifluoromethylphenyl) piperazine), SDZ (−) 21009 (4(3-terbutylamino-2-hydroxypropoxyl)indol-2-carbonic-acid-isopropylester), and butotenine.

IFN-α and histamine/serotonin can be administered separately or in the same preparation. The method of administration can be either local or systemic injection or infusion. Other methods of administration can also be suitable.

The compounds can even be administered intraperitoneally or in another parenteral method. Solutions of the active compounds in the form of free acids or pharmaceutically acceptable salts can be administered in water with or without a tenside such as hydroxypropylcellulose. Dispersions making use of glycerol, liquid polyethyleneglycols, or mixtures thereof with oils can be used. Antimicrobial compounds can also be added to the preparation.

Injectable preparations may include sterile water-based solutions or dispersions and powders that can be dissolved or suspended in a sterile medium prior to use. Carriers such as solvents or dispersants containing, e.g., water, ethanolpolyols, vegetable oils and the like can also be added. Coatings such as lecithin and tensides can be used to maintain suitable fluidity of the preparation. Isotonic substances such as sugar or sodium chloride can also be added, as well as products intended to retard absorption of the active ingredients, such as aluminum monostearate and gelatin. Sterile injectable solutions are prepared in the familiar way and filtered before storage and/or administration. Sterile powders can be vacuum-dried or freeze-dried from a solution or suspension.

All substances added to the preparation must be pharmaceutically acceptable and essentially nontoxic in the quantities used. The preparation and formulations that produce a delayed release are also part of the invention.

The preparation is supplied in dosage units for a uniform dosage and to facilitate administration. Each dosage unit contains a predetermined quantity of active components to produce the desired therapeutic effect, along with the requisite quantity of pharmaceutical carriers.

IFN-α can be administered in a quantity of around 1000 to 300,000 U/kg/day, preferably around 3000 to 100,000 U/kg/day and best of all around 10,000 to 50,000 U/kg/day.

The compounds with $H_2$, and 5-$HT_{1A}$ receptor agonist activity can be administered in a quantity of around 0.1 to 10 mg/day, preferably around 0.5 to 8 mg/day and best of all around 1 to 5 mg/day. However other quantities can be administered with IFN-α, as decided by the treating physician. For substances other than biogenic amines with corresponding receptor activity, doses producing an equivalent pharmacological effect shall be used. Although it is stated in the examples that the administration was given in a single dose, it is obvious that the compounds can be distributed over longer periods of time for treatment of virus infections or tumors.

The daily dose can be administered as a single dose or it can be divided into several doses, should negative effects occur.

EXAMPLES

In Vitro Studies of IFN-α and histamine/serotonin.

The example illustrates the effect of human recombinant IFN-α and histamine/serotonin, separately and in combination, on the NK cell cytotoxicity (NKCC) for human mononuclear cells (MNC).

MNC are obtained from peripheral venous blood from healthy human blood donors by Ficoll-Hypaque centrifuging, followed by Percoll density-gradient fractionation (Timonen and Saksela, 1980, J. Immunol. Methods 36, 285–291; Hellstrand and Hermodsson, 1990, Scand. J. Immunol. 31, 631–645).

In the respective Percoll fractions, the high-density MNC (Percoll fractions 1–4) were small lymphocytes with low baseline cytotoxicity against K562 target cells. After removal of the monocytes, the low-density fractions 6–10 displayed high NKCC, consistent with earlier studies. (Timonen and Saksela, 1980, J. Immunol. Methods 36, 285–291)

The target cells used in these experiments were K562, an NK-cell-sensitive erythroleukemic cell line, or Daudi, a relatively NK-insensitive EBV-transformed B-cell lymphoblastoid cell line.

The NKCC was determined six times as the specific $^{51}$Cr-release for a MNC:target-cell ratio of between 30:1 and 3.8:1 in two-fold dilution gradients. The suspensions of MNC/target cells were incubated in microplates at 37° C. for 6 hours (Daudi) or 16 hours (K562). The supernatant solution was then collected and examined for radioactivity in a gamma counter. The maximum $^{51}$Cr-release was measured in target cell cultures treated with Triton X-100. The NKCC was calculated as the cell lysis % by the formula 100 ×(experimental release—spontaneous release/maximum release—spontaneous release)=cell lysis %.

A low-density Percoll fraction was separated by counterflow centrifuge elution (CCE) in a monocyte and in a lymphocyte fraction. The monocyte fraction was concentrated to >90% purity whereupon the contaminating cells consisted of large lymphocytes. The lymphocyte fractions obtained by CCE contained <3% monocytes, determined by morphology and Leu-M3 (CD14) antigen expression. The lymphocytes were CD3$^-$/16$^+$/56$^+$ T cells (45–50%), CD3$^-$/16$^-$/56$^-$ NK cells (35–40%), CD3$^+$/16$^-$/56$^-$ T cells (45–50%), CD3$^+$/16$^+$/56$^+$ cells (1–5%), determined by flow cytometry.

The eluted monocytes and/or the NK cell-concentrated low-density lymphocytes were treated with IFN-α and histamine/serotonin. The compounds were added, separately or in combination, to mixtures of MNC and K562 target cells at the start of a 16-hour $^{51}$Cr-release assay. The cytotoxicity against K562 in the NK cell-concentrated lymphocyte fraction was increased by IFN-α and unaffected by histamine or serotonin. The eluted monocyte fraction exhibited a low baseline cytotoxicity and was slightly induced by histamine/IFN-α or serotonin/IFN-α; this cytotoxicity resulted from the low fraction of contaminating lymphocytes (data not given). The addition of eluted monocytes to the NK cell-concentrated lymphocytes suppressed the baseline cytotoxicity to K562. Furthermore, the eluted monocytes almost totally inhibited the activation of the cytotoxicity by means of IFN-α (Table 1).

Histamine and serotonin restored the basal cytotoxicity of lymphocytes in mixtures of monocytes and lymphocytes. Furthermore, both histamine and serotonin eliminated the monocyte induced inhibition of the NK cell response to IFN-α. Hence, IFN-α plus histamine or serotonin synergistically enhance the cytotoxicity in mixtures of monocytes and NK cell-enriched lymphocytes (Table 1).

In the experiments reported in Table 1, eluted lymphocytes were mixed with monocytes as shown in the table, in a total volume of 150 μl. The data are NKCC (mean ±SEM) of six determinations. Serotonin $10^{-4}$M and/or IFN-α (25 U/ml) was added at the start of a 16-hour microcytotoxicity test against $10^4$ K562 target cells.

and IFN-α (25 U/ml) produced a synergistic NK-boosting response against K562 and against Daudi target cells. A similar result was obtained when histamine was replaced by serotonin.

In the result shown in Table 2, MNC from five different donors were used. All compounds were added to mixtures of MNC and target cells at the start of a 6 h (Daudi) or 16 h (K562) effector and target cell incubation. The effector cells were obtained from Percoll fractions 7–8, containing 33–55% monocytes.

FIG. 1 shows the synergistic NK cell activation by IFN-α and histamine/serotonin for different concentrations of IFN-α (0–100 U/ml). Cells from the monocyte-containing Percoll fraction 8 were incubated with culture medium, histamine ($10^{-4}$M) or serotonin ($10^{-4}$M) in the presence of IFN-α (0–100 U/ml). The data shown are NKCC (cell lysis %; mean ±SEM of six determinations). The compounds were added at the start of a 16 h microcytotoxicity test against K 562 target cells.

TABLE 2

Synergistic Activation of NK Cells by Histamine and IFN-α

| Exp. | target cell | MNC/target cell ratio | treatment | NKCC (cell lysis % ± SEM) Histamine concentration | | | |
|---|---|---|---|---|---|---|---|
| | | | | 0 | $10^{-4}$M | $10^{-5}$M | $10^{-6}$M |
| 1 | K 562 | 15:1 | Medium | 33.1 ± 0.5 | 55.5 ± 1 | 54.7 ± 1 | 39.2 ± 1 |
| | | | IFN 25 U/ml | 33.1 ± 1 | 76.4 ± 3 | 74.1 ± 1 | 66.0 ± 2 |
| 2 | K 562 | 15:1 | Medium | 20.7 ± 0.4 | 32.4 ± 1 | 27.4 ± 1 | 23.2 ± 2 |
| | | | IFN 25 U/ml | 27.4 ± 1 | 67.9 ± 2 | 66.2 ± 1 | 55.4 ± 1 |
| 3 | K 562 | 15:1 | Medium | 31.4 ± 1 | 43.3 ± 1 | 38.6 ± 1 | 29.4 ± 1 |
| | | | IFN 25 U/ml | 32.5 ± 1 | 71.9 ± 1 | 66.5 ± 2 | 56.3 ± 2 |
| 4. | Daudi | 30:1 | Medium | 1.0 ± 0.4 | 4.4 ± 1 | 3.5 ± 1 | 1.1 ± 0.3 |
| | | | IFN 25 U/ml | 1.1 ± 0.5 | 31.7 ± 1 | 28.3 ± 1 | 14.1 ± 1 |
| 5. | Daudi | 30:1 | Medium | 2.2 ± 1 | 13.5 ± 1 | 9.7 ± 1 | 2.5 ± 1 |
| | | | IFN 25 U/ml | 2.7 ± 1 | 61.3 ± 3 | 52.3 ± 2 | 31.7 ± 1 |

TABLE 1

Suppression of NK Cell Cytotoxicity by Monocytes and Elimination of This Effect with Serotonin
NK CELL CYTOTOXICITY AFTER TREATMENT WITH

| Monocytes (× $10^{-4}$) | Lymphocytes (× $10^{-4}$) | Control | Serotonin | IFN | Serotonin + IFN |
|---|---|---|---|---|---|
| 0 | 12 | 34 ± 1 | 34 ± 3 | 58 ± 3 | 60 ± 2 |
| 6 | 12 | 10 ± 2 | 31 ± 2 | 17 ± 1 | 52 ± 2 |
| 12 | 12 | 9 ± 1 | 31 ± 2 | 10 ± 1 | 52 ± 2 |

Table 2 shows the synergistic activation of NK cells by combined treatment with IFN-α and histamine. Monocytes were recovered along with NK cells in low-density Percoll fractions. In the experiment shown in Table 2, IFN-α and/or histamine was added to MNC obtained from these monocyte-containing Percoll fractions. As was the case with mixtures of eluted monocytes and low-density lymphocytes, IFN-α was relatively ineffective in these cell fractions, while histamine increased the cytotoxicity. Treatment of monocyte-containing cells with histamine ($10^{-4}$–$10^{-6}$M)

The effect of histamine on monocyte-induced suppression of resting and IFN-α-activated NK cells was completely blocked by simultaneous treatment with the specific $H_2R$ antagonist ranitidine and imitated by the $H_2R$ agonist dimaprit, which is shown in Table 3. This means that the effect of histamine on the NK cell's response to IFN-α is $H_2R$-specific.

TABLE 3

Effects of Histamine and $H_2R$ Agonist Dimaprit and $H_2$-Antagonist Ranitidine on NK Cells
NKCC (Cell Lysis %) ± SEM After Treatment With

| Treatment | Control | Ran | IFN | Ran + IFN |
|---|---|---|---|---|
| Control | 0.1 ± 0.1 | 0.0 ± 0.1 | 0.1 ± 0.1 | 0.0 ± 0.1 |
| Histamine | 9.4 ± 0.3 | 1.5 ± 0.3 | 31.7 ± 0.3 | 1.6 ± 0.2 |
| Dimaprit | 6.4 ± 1 | 0.4 ± 0.4 | 32.6 ± 1 | 0.5 ± 0.5 |

In the experiment shown in Table 3, culture medium (control), histamine ($10^{-4}$M), dimaprit ($10^{-4}$M), ranitidine (ran) ($10^{-4}$M) and/or IFN-α (25 U/ml) were added at the start of a 6-hour $^{51}$Cr-release assay using Daudi target cells. The data are representative of three similar experiments. NKCC is given as mean cell lysis %±SEM of six determinations. The effector cells were recovered from a low-density Percoll fraction 8, containing around 40% monocytes.

Serotonin acted synergistically with IFN-α and had an effect corresponding to that of histamine. Ranitidine (10⁻⁴M) did not alter the effect of serotonin. The specific synthetic 5-HT$_{1A}$R-agonists 8-OH-DPAT and (+)-ALK-3, which lack activity for 5-HT$_{1B}$R, 5-HT$_{10}$R, 5-HT$_2$R or 5-HT$_3$R, intensified the baseline NKCC and restored the NK cell's response to IFN-α with a potency and effect comparable to that of serotonin. This is shown by Table 4. Ketanserin and ondansetron, which are antagonists of 5-HT$_2$R and 5-HT$_3$R, respectively, did not influence the effect of serotonin in equimolar concentrations.

TABLE 4

The Effect of Serotonin and 5-HT$_{1A}$R Agonists on NK Cells

| Treatment | NKCC After Treatment With | |
|---|---|---|
| | Medium | IFN |
| Medium | 1.1 ± 1 | 0.5 ± 0.3 |
| Serotonin 10⁻⁴ M | 10.4 ± 1 | 44.3 ± 1 |
| Serotonin 10⁻⁵ M | 4.5 ± 0.03 | 33.2 ± 1 |
| Serotonin 10⁻⁶ M | 2.2 ± 0.4 | 12.3 ± 1 |
| 8-OH—DPAT 10⁻⁴ M | 8.8 ± 1 | 43.3 ± 1 |
| (+)-ALK-3 10⁻⁴ M | 9.1 ± 1 | 40.4 ± 1 |

In the experiment shown in Table 4, culture medium (control), serotonin, 8-OH-DPAT (+)-ALK and/or IFN-α (25 U/ml) were added at the start of a 6-hour ⁵¹Cr-release assay against Daudi target cells. The NKCC is given as cell lysis %±SEM of six determinations. The effector cells were recovered from the low-density Percoll fraction 7, containing around 36% monocytes.

Similar experiments were then performed using freshly recovered human tumor cells as target cells, rather that the cultured tumor cell lines used as target cells in the experiments described above.

MNC were obtained from peripheral venous blood by Ficoll-Hypaque centrifuging and the mononuclear cells were separated into monocytes and NK-cell-enriched lymphocytes (Hellstrand et al., J. Interferon Res., 12, 199–206 1992). Seventy thousand NK-cell-enriched lymphocytes were mixed with 70,000 monocytes and 20,000 ⁵¹Cr-labeled leukemic target cells (97% pure acute myelogenous leukemic cells) in a total volume of 150 μl. The cells were treated with culture medium (control) or histamine dihydrochloride at a final concentration of 10⁻⁴M, during a 16 hour ⁵¹Cr-release assay to determine killed target cells.

Figure 2:
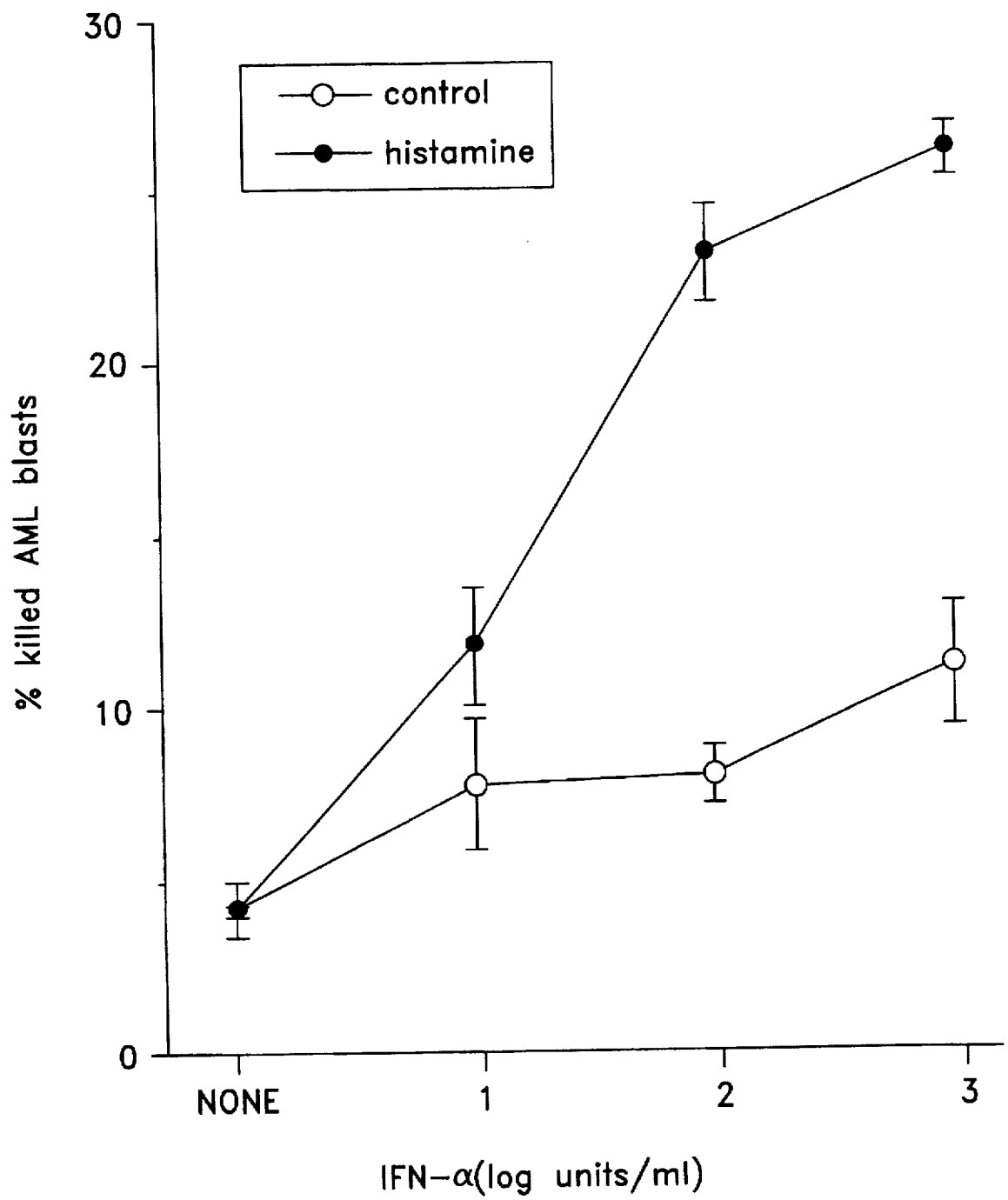
FIG. 2 shows in graph form the synergistic NK cell activation produced against freshly recovered human leukemic cells by IFN-α and histamine for various concentrations of IFN-α (0–100 U/ml).

The results are shown in FIG. 2. The data are the mean percent cell lysis of six determinations±SEM. The recorded cytotoxicity was completely depleted after removal of NK-cells using DYNABEADS coated with anti-CD56, but not by removal of T-cells using beads coated with anti-CD3 (Hellstrand et al., Scand. J. Immunol., 37:7–18 (1993). As seen in FIG. 2, treatment with interferon alone does not induce killing of leukemic target cells unless histamine is present. In addition, it has been shown that the cytotoxic effects obtained with histamine and interferon-α are seen not only in cultured tumor cells, but in freshly recovered human leukemic cells as well.

Thus, in conclusion, it can be affirmed that the above-described in vitro experiments demonstrate that the biogenic amines histamine, through H$_2$-type receptors, and serotonin, through 5-HT$_{1A}$-type receptors, abolish the monocyte-induced suppression of resting and IFN-α activated NK cells. Treatment with IFN-α and compounds with H$_2$ or HT$_{1A}$ receptor agonist activity thus produces a synergistic activation of NK cells, which can be used in connection with tumor treatment or treatment of virus infections.

We claim:

1. A composition for the synergistic activation of natural killer cells (NK cells) in the presence of monocytes, comprising a first composition containing interferon-α and a second composition containing at least one compound having affinity and agonist activity for histamine H$_2$ or serotonin 5-HT$_{1A}$ receptors.

2. The composition of claim 1, wherein said interferon-α is present in an amount between about 1000 and 300,00 U/kg.

3. The composition of claim 1, wherein said second composition is present in an amount between about 0.1 and 10 mg.

4. The composition of claim 1, wherein said at least one compound is selected from the group consisting of histamine, serotonin, dimaprit, clonidine, tolazoline, impromadine, 4-methylhistamine, betazole, a histamine congener, 8-hydroxy-2-(di-n-propylamino)tetralin, cis-8-hydroxy-1-methyl-2-(di-n-propylamino)tetralin, 8[2-[4-(2-methoxyphenyl)-1-piperazinlyethyl]-8-azaspiro[4,5] decane-7,9-dione, 1-(2-methoxyphenyl)-4-[4-(2-phthalimido)butyl]piperazine HBr, lisuride, d-LSD, flesoxinan, dihydroergotamine, 8-[4-(1,4-benzodioxan-2-ylmethyl-amino)butyl]-8-azaspiro[4,5] decane-7,9-dione, 5-carboxamidotryptamine, N,N-dipropyl-5-carboxamidotryptamine, ipsapirone, 2-[[[2-(2,6-dimethoxyphenoxy)ethyl]amino]methyl]-1,4-benzodioxane, ergotamine, buspirone, metergoline, spiroxatrine, 1-[2-(4-aminophenyl)ethyl]-4-(3-trifluoromethylphenyl) piperazine, 4(3-terbutylamino-2-hydroxypropoxy)indol-2-carbonic-acid-isopropylester, and butotenine.

5. The composition of claim 1, further comprising a pharmaceutically acceptable carrier.

6. The composition of claim 1, wherein said at least one compound is selected from the group consisting of:

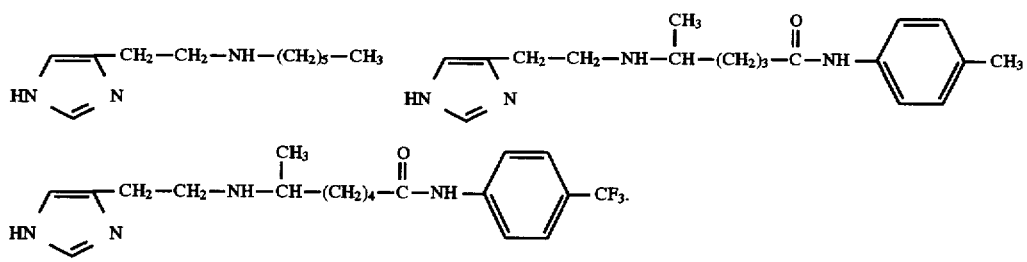

7. A method for the synergistic activation of natural killer cells (NK cells) in the presence of monocytes, comprising:

administering a first composition containing interferon-α and administering a second composition containing at least one compound having affinity and agonist activity for histamine H$_2$ or serotonin 5-HT$_{1A}$ receptors.

8. The method of claim 7, wherein said administering steps are performed in vitro.

9. The method of claim 7, wherein said administering steps are performed in vivo.

10. The method of claim 7, wherein said first and second compositions are administered together.

11. The method of claim 7, wherein said first and second compositions are administered separately.

12. The method of claim 7, wherein said interferon-α is administered in a daily dose of between 1000 and 300,000 U/kg.

13. The method of claim 7, wherein said second composition is administered in a daily dose of between 0.1 and 10 mg.

14. The method of claim 7, wherein said at least one compound is selected from the group consisting of serotonin, histamine, dimaprit, clonidine, tolazoline, impromadine, 4-methylhistamine, betazole, a histamine congener, 8-hydroxy-2-(di-n-propylamino)tetralin, cis-8-hydroxy-1-methyl-2-(di-n-propylamino)tetralin, 8[2-[4-(2-methoxyphenyl)-1-piperazinyl]ethyl]-8-azaspiro[4,5] decane-7,9-dione, 1-(2-methoxyphenyl)-4-[4-(2-phthalimido)butyl]piperazine, lisuride, d-LSD, flesoxinan, dihydroergotamine, 8-[4-(1,4-benzodioxan-2-ylmethylamino)butyl]8-azaspiro[4,5] decane-7,9-dione, 5-carboxamidotryptamine, N,N-dipropyl-5-carboxamidotryptamine, ipsapirone, 2-[[[2-(2,6-dimethoxyphenoxy)ethyl]amino]methyl]-1,4-benzodioxane, ergotamine buspirone, metergoline, spiroxatrine, 1-[2-(4-aminophenyl)ethyl]-4-(3-trifluoromethylphenyl) piperazine, 4(3-terbutylamino-2-hydroxypropoxy)indol-2-carbonic-acid-isopropylester, and butotenine.

15. The method of claim 14, wherein the histamine congener is selected from the group consisting of:

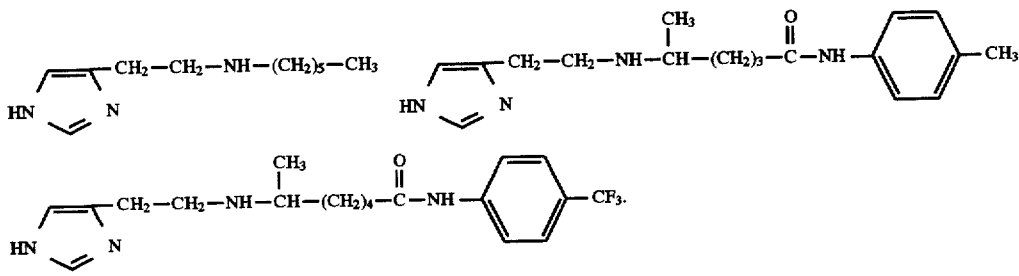

* * * * *

UNITED STATES PATENT AND TRADEMARK OFFICE
CERTIFICATE OF CORRECTION

PATENT NO. : 5,728,378
DATED : March 17, 1998
INVENTOR(S) : Hellstrand et al.

It is certified that error appears in the above-identified patent and that said Letters Patent is hereby corrected as shown below:

In Claim 1, column 8, line 17: please replace "ceils", with - - cells - -

In Claim 2, column 8, line 23: please replace "300,00", with - - 300,000 - -.

Signed and Sealed this

Twenty-third Day of March, 1999

Attest:

Q. TODD DICKINSON

*Attesting Officer*            *Acting Commissioner of Patents and Trademarks*